(12) United States Patent
Patch

(10) Patent No.: US 6,264,365 B1
(45) Date of Patent: Jul. 24, 2001

(54) BACKGROUND MONITORING OF CT DATA FOR EXISTENCE AND LOCATION OF A BAD DETECTOR

(75) Inventor: Sarah Kathryn Patch, Milwaukee, WI (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/425,309

(22) Filed: Oct. 25, 1999

(51) Int. Cl.[7] .................................................. H05G 1/00
(52) U.S. Cl. ............................ 378/204; 370/20; 250/252.1
(58) Field of Search .................................... 378/207, 204, 378/20; 250/252.1

(56) References Cited

U.S. PATENT DOCUMENTS

| | | | |
|---|---|---|---|
| 4,712,178 | * 12/1987 | Tuy et al. | 364/414 |
| 4,812,983 | 3/1989 | Guillberg et al. . | |
| 4,815,816 | * 3/1989 | Schneider | 350/96.25 |
| 4,951,222 | * 8/1990 | Hoffman et al. | 364/507 |
| 5,091,862 | * 2/1992 | Hoffman et al. | 364/507 |
| 5,208,746 | 5/1993 | King et al. . | |
| 5,228,934 | * 7/1993 | Mattson et al. | 364/413.21 |

OTHER PUBLICATIONS

G. Glover & R.L. Eisner, "Consistent Projection Sets: Fan Beam Geometry", in Computer Aided Tomography and Ultrasonics in Medicine (1991), pp. 235–251.

\* cited by examiner

*Primary Examiner*—David V. Bruce
*Assistant Examiner*—Pamela R. Hobden
(74) *Attorney, Agent, or Firm*—Donald S. Ingraham; Douglas E. Stoner

(57) ABSTRACT

A monitoring apparatus analyzes detector data from a CT system to detect a signature of a bad detector. The apparatus generates a plurality of Helgason-Ludwig condition values from the detector data. The generated values are processed to generate a comparison value, which is compared to a predetermined threshold value. A warning message may be generated when the comparison value exceeds the predetermined threshold value, the warning message alerting an operator to the likely presence of a bad detector. In one embodiment, the generated values are further analyzed to generate an estimate of the position of the bad detector. In a preferred embodiment, the comparison value is a matrix norm of a matrix generated from the Helgason-Ludwig condition values.

49 Claims, 4 Drawing Sheets

BACKGROUND MONITORING OF CT DATA FOR EXISTENCE AND LOCATION OF A BAD DETECTOR

BACKGROUND OF THE INVENTION

This invention relates to computerized tomography and, more particularly, to monitoring for the existence and location of a faulty detector in a detector array of a computerized tomography system.

Computerized tomography (CT), or "computed tomography," is an imaging technology in which an array of detectors generate data from energetic rays transmitted through or emitted from an imaging object. For example, a transmission-type medical CT imaging system uses an array of x-ray detectors to detect an attenuated x-ray beam that has passed through the body of a human or animal subject. The detector data are processed by a computer system to generate image data representing a recognizable view of the interior structure of the imaging object.

CT techniques are valuable in a wide range of application areas where noninvasive and nondestructive examination of internal structures is needed. Medical applications include imaging of emissions from radioactive substances introduced into the subject (single photon emission CT, positron emission CT, etc.), as well as x-ray transmission CT. Non-medical applications include, for example, non-destructive testing and inspection, mineral deposit mapping (microseismic CT imaging), and three-dimensional image generation in electron microscopy.

A CT system generates a display image from data representing measurements of energetic signals transmitted through or emitted from a subject in a range of directions. This process is "tomographic" in that structural details of a subject are represented as a cross-sectional view along a given plane through the subject. The process is "computerized" because the raw detector data only indirectly represent a view of the subject. Substantial data processing is required to convert the raw data into a recognizable view of the internal features of the subject.

Computer processing of CT detector data is necessary because the data correspond to mere projections of the subject structure along various different paths. The differences between the data along different paths, in relation to the spatial separation of the paths, provide an indirect representation of the interior structure of the subject. However, to obtain a recognizable view of that structure requires processing of the projection data from the detectors by a so-called reconstruction algorithm.

The image data representing a CT image are therefore the product of considerable computer processing applied to projection data collected by the detector array. This indirect relationship between image data and detector data distinguishes CT imaging from direct photographic imaging technologies. For example, a charge-coupled device (CCD) camera comprises an array of solid state photosites each detecting incident radiation (such as visible light) at a corresponding position. Such a camera produces an image in which each picture element ("pixel") directly corresponds to a photosite in the CCD array.

In contrast, a CT system produces images in which each pixel is reconstructed from data generated by many detectors. The image data representing the image therefore do not correspond directly to individual detectors in the detector array. Instead, each image pixel will typically include contributions from the projection data of all the detectors in the system.

The indirect relationship between image data and detector data seriously complicates the problem of recognizing the presence of a faulty detector in a CT system. The presence of a bad photosite in a CCD camera will generally be apparent from localized artifacts in the CCD image. In a CT image, however, the relationship between a bad detector and an image artifact caused by the bad detector is less direct. This is because the CT image has been generated through a reconstruction algorithm, which has combined the bad detector data together with the data from the other detectors in the detector array.

In current CT systems, constructed according to the existing third-generation architecture (to be described below), the existence of a bad detector shows up in the CT image as a so-called "ring" artifact. Trained CT technicians can readily identify such ring artifacts in a generated CT image. The location of the ring in the image will also typically provide some information about the location of the bad detector in the detector array.

Reliance on ad hoc visual inspection, however, leaves much to be desired for reliable and repeatable identification of bad CT detectors. Fourth generation systems currently under development are expected to avoid generating the ring artifacts upon which such inspection depends. Even for current systems, the reliability of visual inspection depends on the care and accuity with which individual CT images are inspected.

Moreover, current CT systems typically implement post-processing techniques to remove ring artifacts. These techniques reduce the local image distortion caused by the ring, but they also inevitably cause a loss of some relevant image information. The local image distortion of the ring artifact is also the image feature that makes the existence of a bad detector discernable by visual inspection of the image. Thus, post-processing to clean up CT images has the unfortunate side effect of making the existence of a bad detector even more difficult to identify.

In view of these problems, users of CT systems need a practical system and method for detecting the existence and location of a bad detector in a CT detector array. Such a system should provide reliable, repeatable monitoring of the detector data to determine whether the data contains a signature indicative of a bad detector. Preferably, such a system would perform its monitoring function in a background mode transparent to the normal operation of the CT system. Ideally, the monitoring system would alert a responsible party to the likely presence of a bad detector and would also estimate the position of the bad detector in the detector array.

SUMMARY OF THE INVENTION

The present invention meets these needs by providing, in a first aspect, an apparatus for monitoring detector data of a CT system to detect a bad detector, the apparatus comprising a processing unit that processes the detector data to generate a plurality of Helgason-Ludwig condition values, generates a comparison value from the Helgason-Ludwig condition values, and compares the comparison value to a predetermined threshold value. The apparatus further comprises a notifying unit that generates a notification signal when the comparison value exceeds the predetermined threshold value.

In a second aspect, the invention provides a computed tomography system comprising a detector array and a computer. The detector array generates detector data responsive to energetic signals attenuated by a signal-absorbing body.

The computer includes a processor for processing the detector data to generate a plurality of Helgason-Ludwig condition values, generates a comparison value from the Helgason-Ludwig condition values, and comparing the comparison value to a predetermined threshold value. The computer generates a notification signal when the comparison value exceeds the predetermined threshold value.

BRIEF DESCRIPTION OF THE DRAWING FIGURES

DETAILED DESCRIPTION OF THE INVENTION

A first embodiment of the invention will be described with reference to a typical third-generation transmission CT system. However, in view of the following disclosure, it will be apparent that the same basic principles also apply, and similar results obtain, in a variety of related contexts for computerized tomography, such as so-called "fourth generation" transmission CT systems as described below.

This detailed description is organized according to the following outline:

0. Structure of a CT System
1. Theoretical Framework
   a. Derivation of the H-L Range Conditions in Parallel Beam Notation
   b. Conversion of the H-L Conditions to Fan-Beam Notation
2. Signature Detection
   a. Derivation of the "Signature" of a Bad Detector
   b. A System for Signature Detection
3. Alternative Embodiments The present invention uses principles provided by the derivation of a bad-detector signature, as described in Part 2.a. below. The system and method of Part 2.b. implement those principles for monitoring CT systems for bad detectors.

0. Structure of a CT System

Figure 1:
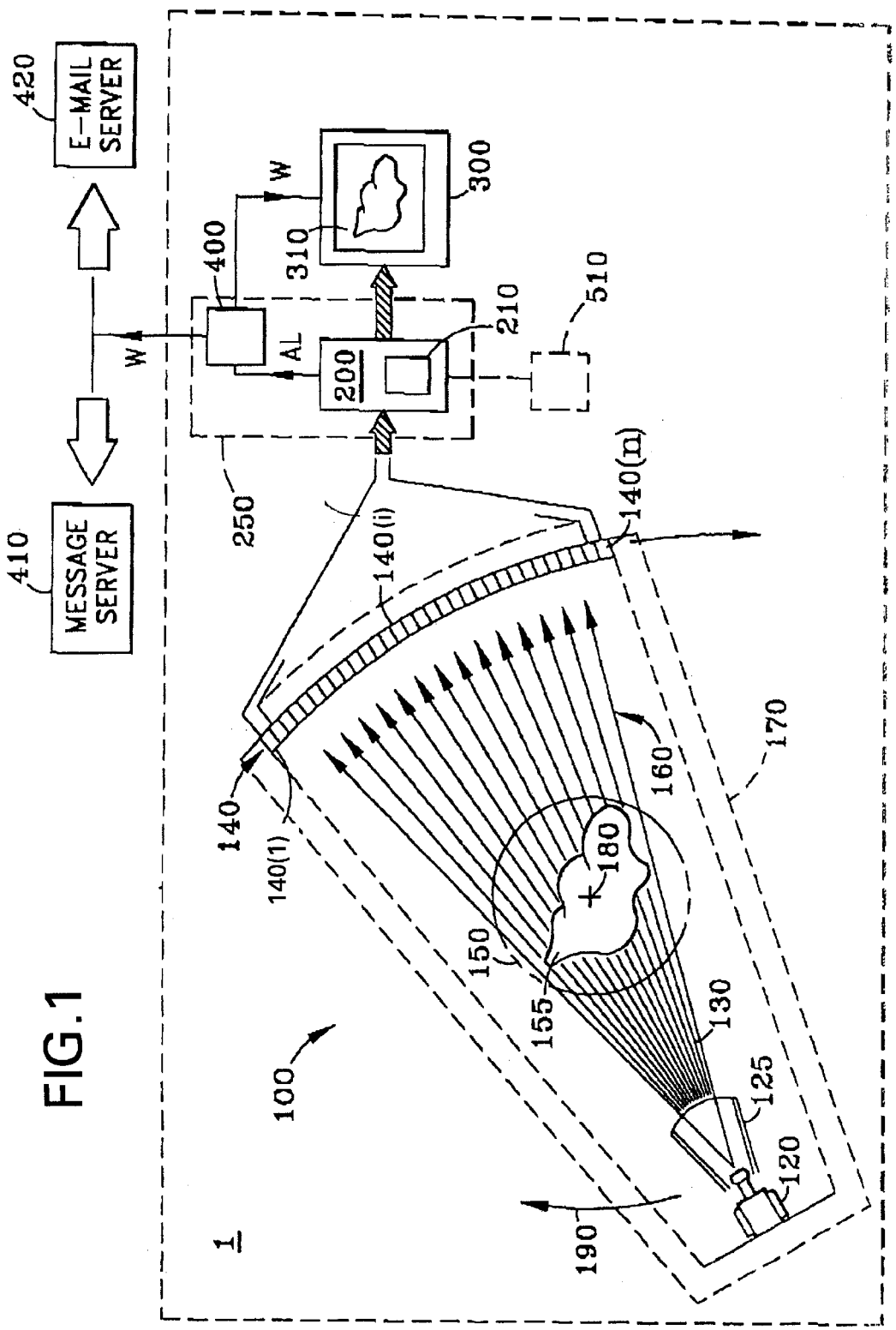
FIG. 1 illustrates a CT system embodying the present invention.

FIG. 1 is a schematic illustration showing the major structural features of a CT imaging system 1 incorporating the present invention. The CT system 1 of FIG. 1 includes a source-detector assembly 100, which comprises an X-ray source 120 such as a typical X-ray tube. A collimating element 125 shapes the radiation pattern emitted from source 120 into a thin, fan shaped beam of radiation 130. Here, "thin" refers to the direction transverse to the fan plane. Fan beam 130 impinges on a detector array 140 comprised of numerous individual detectors 140(1)–140(n). An alternative term in the art for an array such as detector array 140 is "a multi-channel detector." It will be understood that either term is intended to mean a multiple-channel detection device usable in a computed tomography system.

Interposed between collimating element 125 and array 140 is a subject aperture 150 within which an imaging object 155, such as a human patient, is positioned. Fan beam 130 passes through object 155 and is thereby attenuated. Rays 160 of attenuated beam 130 impinge on detectors 140(1)–140(n), which thereby generate detection signals indicative of the relative densities of internal structures within object 155.

FIG. 1 illustrates the particular case of a so-called third generation CT system, in which source 120, collimating element 125, and detector array 140 are fixed to a gantry structure 170 (represented by phantom lines). A typical detector array 140 may comprise several hundred individual detectors 140(i) arranged on one side of gantry 170 in a circular arc with center at source 120. In operation, assembly 100 rotates about an axis 180 passing through object 155 and perpendicular to the plane of FIG. 1. Source 120 can thereby be transported completely around object 155 along a circular path 190. Detector array 140, being fixed with respect to source 120, is also transported around object 155 and thus remains opposite source 120. Here, "third generation" means the detector assembly and the source are rotationally fixed with respect to one another, although each rotates about an axis of rotation.

A typical system as depicted in FIG. 1 has, for example, 888 detectors (i.e., n=888) positioned on gantry 170 at a distance of 0.949 meters (m) from source 120. The circular path 190 of source 120 has a radius of, for example, 0.541 m. Particular values of these parameters are not critical to the present invention and may be varied according to well-known principles of CT system design.

In this exemplary system, assembly 100 may rotate through one complete rotation in, for example, 984 increments. Source 120 is thereby positioned to illuminate object 155 successively from 984 different directions. Detector array 140 generates data at each incremental position and thereby generates detector data for 984 sets of projections (or views).

The system 1 of FIG. 1 further includes a reconstruction unit 200 coupled to the detectors 140(1)–140(n) and comprising a processing unit or processor 210. Processor 210 is configured, typically through software, to process the detector data for a given axial position of the source-detector assembly 100. The detector data (e.g., 888×984 detector data) are processed according to any of various CT reconstruction techniques well known in the art, and image data are generated therefrom to represent an axial image representing a cross-sectional view of object 155 at the given axial position. Such CT reconstruction techniques are described in, for example, U.S. Pat. No. 4,812,983, issued Mar. 14, 1989, to Gullberg, et al. The collection of detector data for a single such image is referred to as "axial scan data" or simply an "axial scan."

The generated image data can then be transferred to an image display unit 300, which may be a video display, for example. Display unit 300 generates a visible presentation 310 of the axial image. In a case where the display unit 300 is a video display, the visible presentation 300 is a video picture, for example. Alternatively the display unit 300 may be a film imager that generates the visible presentation 310 as a film image on a radiographic film or on other visual recording film medium.

The present invention provides a system and method for monitoring image quality from the axial scan data, rather than from visual inspection of the visible presentation 310 of the generated image. This is possible because the axial scan data for a tomographic image are related as projections along co-planar paths. In particular, the CT detector data approximate line integrals of the imaging object's linear attenuation coefficient along respective source-detector paths.

The fact that axial scan data are a collection of related projections means that such data will, in theory, satisfy the so-called Helgason-Ludwig ("H-L") range conditions. The H-L conditions are known to be necessary and sufficient conditions for invertibility of the Radon transform. See, e.g., S. HELGASON, THE RADON TRANSFORM (1980), and H. DYM & H. P. MCKEAN, FOURIER SERIES AND INTEGRALS (1972). The H-L conditions have been used in NMR imaging to help remove artifacts caused by patient motion. See, e.g., G. Glover & R. L. Eisner, Consistent Projection Sets. Fan Beam Geometry, in COMPUTER AIDED TOMOGRAPHY AND ULTRASONICS IN MEDICINE 235–251 (1991).

If the fan beam is monoenergetic, then the exact value of the linear attenuation coefficient at a given point would be the object density at that point. Naturally, effects such as scattering, beam hardening, and measurement discretization cause errors in the linear attenuation coefficient approximation. Such errors are "global" in nature, i.e., are non-systematic with respect to individual detector data. Global errors cause violations of the H-L conditions, but such violations are randomly distributed and cause uniformly distributed errors among the H-L conditions.

Unlike the sources of global errors, a single bad detector in a CT system will produce errors that are localized in terms of position within the fan beam. Such errors will generate a recognizable pattern, or "signature," in the axial scan data's violation of the H-L conditions. The present invention applies the H-L conditions to analysis of axial scan data for the presence of systematic errors. This enables the axial scan data to be monitored for both the presence and the location of a faulty detector channel.

1. Theoretical Framework a. Derivation of the H-L Range Conditions in Parallel Beam Notation.

Figure 2:
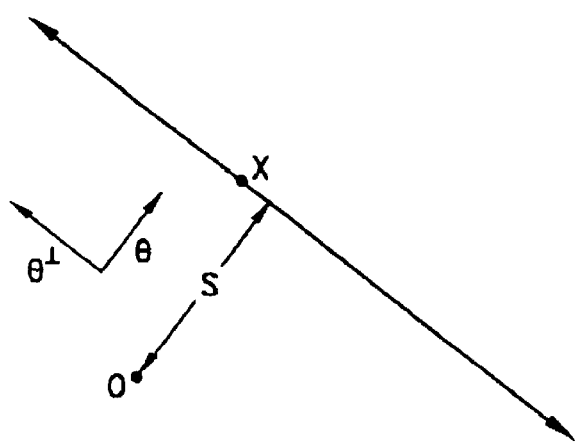
FIG. 2 illustrates the geometry of parallel-beam CT data acquisition.

FIG. 2 illustrates the geometry of the parallel beam coordinate system. As noted above, a CT data value (or more precisely, the natural logarithm of the data value) is a line integral of the imaging object's linear attenuation coefficient. That is, $Rf(\theta,s)$ is the line integral of along the line $\{x|x=s\theta+t\theta^\perp, t\in R^1\}$ (where R denotes the real numbers). This line integral is expressed in parallel-beam coordinates as:

$$Rf(\theta, s) = \int_{x\cdot\theta=s} f(x)dx \text{ where } \theta \equiv (\cos\phi, \sin\phi) \quad (1.1)$$

Here x is the position vector of a point within the object, relative to a point of origin O. The function $f(x)$ represents the attenuation coefficient of the object at the point x. The direction vector $\theta$ defines a particular parallel beam passing through the point x. The scalar s is the (perpendicular) distance from the origin O to the parallel beam defined by $\theta$. Thus, the parallel beam data value $Rf$ is a function of the displacement (s) and the direction ($\theta$) of the parallel beam along which $f(x)$ is integrated.

The H-L range conditions say that the moments of $R\theta$ with respect to s have Fourier series expansions with only finitely many nonzero coefficients. This can be seen most conveniently by expressing x in polar coordinates $(r,\phi)$, whereby $\theta$ $(\cos\phi, \sin\phi)$. For m=0, , 2, . . . , $$\int_R s^m Rf(\theta, s)ds = \int_R s^m \int_{x\cdot\theta=s} f(x)d^1 x ds \quad (1.2)$$
$$= \int_R \int_{x\cdot\theta=s} (x\cdot\theta)^m f(x)d^1 x ds$$
$$= \int_{R^2} (x_1\cos\phi + x_2\sin\phi)^m f(x)d^2 x$$
$$= p_m(\cos\phi, \sin\phi)$$
$$= p_m\left(\frac{1}{2}(e^{i\phi} + e^{-i\phi}), \frac{1}{2i}(e^{i\phi} + e^{-i\phi})\right)$$
$$= \sum_{j=-m}^{m} c_{m,j} e^{ij\phi}$$

where $p_m$ is a homogeneous polynomial of degree m. Equivalently, for each pair k, m satisfying $|k|>m\geq 0$, $$0 \equiv \int_0^{2\pi} e^{ik\phi} \int_R s^m Rf(\theta, s) ds d\phi \quad (1.3)$$

Furthermore, these conditions are known to be sufficient for invertibility of the line integrals to recover the object's linear attenuation as a function of position. This means that if a function $g = g(\theta, s)$ satisfies 1) g is smooth and decays sufficiently fast with respect to s;

2) $g(\theta,s) = g(-\theta,-s)$; and 3) g satisfies the H-L range conditions, then $g=Rf$ for some function $f$.

b. Fan Beam Parameterization

Figure 3:
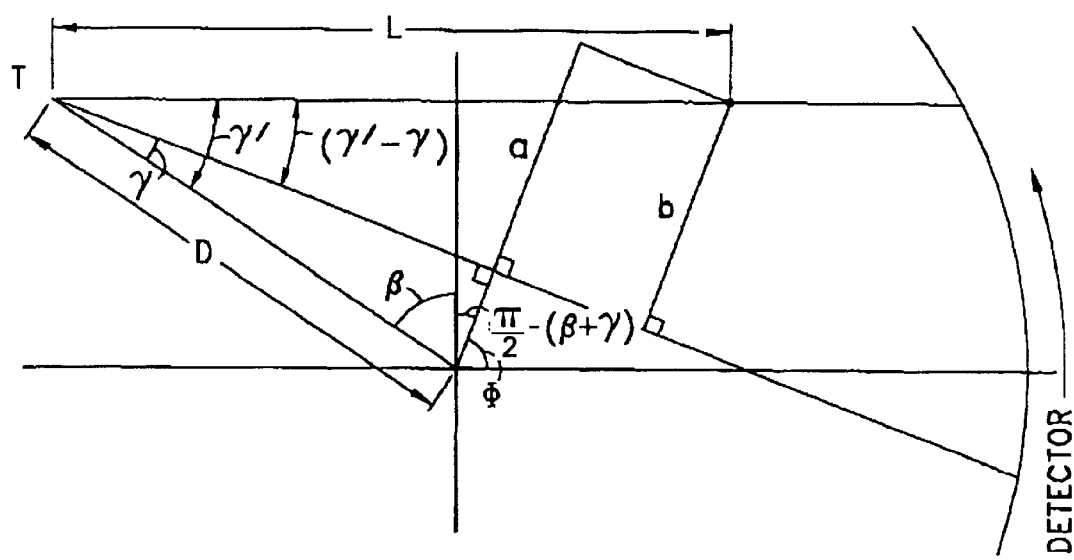
FIG. 3 illustrates the geometry of fan-beam CT data acquisition.

The change of variables from parallel-beam coordinates to fan-beam geometries will now be demonstrated with reference to FIG. 3. Parameter relations between the two coordinate geometries are as follows:

$|S|=D$ $L=|S-x|=L(\beta,x)$

Also, from FIG. 3 it follows that $x\cdot\theta-s=$ length of line segment $a$ $L \sin(\gamma-\gamma')=$ length of line segment $b$ (1.4)

The change of variables from $(s,\theta(\phi))$ to $(\beta,\gamma)$ is simply $s=D\sin\gamma$ where $(s,\phi)\in R^1\times[0,2\pi)$ $(\beta,\gamma)\in[0,2\pi)\times[-\pi/2,\pi/2]$ (1.5)

with Jacobian $$J = \begin{vmatrix} D\cos\gamma & 0 \\ 1 & 1 \end{vmatrix} = D\cos\gamma \quad (1.6)$$

Therefore, the H-L conditions can be rewritten in fan-beam notation, for $|k|>m\geq 0$, as $$Cond(k,m) = \int_0^{2\pi} e^{ik\phi} \int_R s^m Rf(\theta(\phi),s)\,ds\,d\phi \qquad (1.7)$$

$$= \int_{-\pi/2}^{\pi/2} \int_0^{2\pi} e^{ik(\beta+\gamma)}(D\sin\gamma)^m Rf(D\sin\gamma,\beta+\gamma)(D\cos\gamma)\,d\beta\,d\gamma$$

$$= D^{m+1} \int_0^{2\pi} e^{ik\beta} \int_{-\pi/2}^{\pi/2} (\sin\gamma)^m e^{ik\gamma} Tf(D\sin\gamma,\beta+\gamma)\,d\gamma\,d\beta$$

where $Tf$ is the "fan beam" data, which is equal to the "parallel beam" data $Rf$ multiplied by the scaling factor $\cos\gamma$. That is, $$Tf(\beta,\gamma) \equiv \cos\gamma Rf(D\sin\gamma,\beta+\gamma) \qquad (1.8)$$

2. Signature Detection a. Derivation of the "Signature" of a Bad Detector

Suppose that $\hat{T}f$ is measured data, where everything is correct except for one detector at a specific position. In the third-generation CT system of FIG. 1, the detector array 140 is stationary with respect to the fan beam. Therefore, the position of the bad detector can be uniquely determined by a specific fan position $\gamma_0$.

This situation can be modeled by expressing $\hat{T}f$ as $$\hat{T}f(\beta,\gamma) \equiv Tf(\beta,\gamma) + g(\beta)\delta_{\gamma_0}(\gamma) \qquad (2.1)$$

where $Tf$ satisfies the H-L conditions and $g$ is an unknown (but well-behaved) function of $\beta$. To the extent that equation (2.1) provides an effective model, the measured data $\hat{T}f$ will violate the H-L conditions in a highly systematic way. For such measured data $\hat{T}f$, the H-L conditions of equation (1.7) become $$Cond(k,m) = D^{m+1} \int_0^{2\pi} e^{ik\beta} \int_{-\pi/2}^{\pi/2} (\sin\gamma)^m e^{ik\gamma} g(\beta)\delta_{\gamma_0}(\gamma)\,d\gamma\,d\beta \qquad (2.2)$$

$$= D^{m+1} \int_0^{2\pi} e^{ik\beta} \int_{-\pi/2}^{\pi/2} (\sin\gamma)^m e^{ik\gamma} g(\beta)\delta_{\gamma_0}(\gamma)\,d\gamma\,d\beta$$

$$= D^{m+1} \left( \int_0^{2\pi} e^{ik\beta} g(\beta)\,d\beta \right) (\sin\gamma_0)^m e^{ik\gamma_0}$$

$$= G_k(D\sin\gamma_0)^m$$

where $$G_k \equiv De^{ik\gamma_0} \int_0^{2\pi} e^{ik\beta} g(\beta)\,d\beta$$

is again some constant that is unknown but depends only on $k$.

Although the values of the constants $G_k$ are unknown, it has been discovered that the ratios of the non-zero values given by the H-L conditions are related. Here, the "H-L condition values" will mean the values given by the H-L range conditions, i.e., the values given by equations (1.7) or (2.2). For convenience, define the constant $E$ by $$E \equiv D\sin\gamma_0 \qquad (2.3)$$

The relations between the (non-zero) H-L condition values can be expressed as $$\frac{Cond(k,m_1)}{Cond(k,m_2)} = E^{m_1-m_2} \text{ whenever } |k| > \max(m_1,m_2) \qquad (2.4)$$

and

-continued $$\frac{Cond(k_1,m)}{Cond(k_2,m)} = \frac{G_{k_1}}{G_{k_2}} \text{ for } m = 0, 1, \ldots, \min(|k_1|,|k_2|) \qquad (2.5)$$

The significance of these relations can be explained more readily with reference to a "matrix" of H-L condition values for the measured data $\hat{T}f$:

| | $m=0$ | $m=1$ | $m=2$ | $m=3$ | $m=0$ $\cdots$ | (2.6) |
|---|---|---|---|---|---|---|
| $k=1$ | $G_k$ | | | | | |
| $k=-1$ | $G_{-k}$ | | | | | |
| $k=2$ | $G_2$ | $G_2 E$ | | | | |
| $k=-2$ | $G_{-2}$ | $G_{-2}E$ | | | | |
| $k=3$ | $G_3$ | $G_3 E$ | $G_3 E^2$ | | | |
| $k=-3$ | $G_{-3}$ | $G_{-3}E$ | $G_{-3}E^2$ | | | |
| $k=4$ | $G_4$ | $G_4 E$ | $G_4 E^2$ | $G_4 E^3$ | | |
| $k=-4$ | $G_{-4}$ | $G_{-4}E$ | $G_{-4}E^2$ | $G_{-4}E^3$ | | |
| $\vdots$ | $\vdots$ | $\vdots$ | $\vdots$ | $\vdots$ | | |

The present invention takes advantage of several notable features of these H-L condition values. First, if the effects of global errors are ignored, then all of the matrix entries will be identically zero unless the CT system has a bad detector. This fact is a consequence of the basic range condition for projection data, expressed above in equation (1.3). In other words, if the detector data $Tf$ (measured data taken with all detectors working properly) satisfy the H-L conditions, then the matrix of H-L values for $Tf$ will have all zero entries. Only the effect of a bad detector on the data will cause the matrix for the data $\hat{T}f$ to have non-zero entries.

The potential therefore exists to use the presence of non-zero values among the H-L condition values as an indicator of the presence of a bad detector. Preferably, however, a method to realize this potential will involve more than comparing the H-L condition values to zero. This is because, due to the global errors discussed above, real CT systems do not generate perfect data. Other errors are introduced in the process of computing the H-L condition values themselves, through computational discretization error and rounding error. These global and computational errors prevent even "good" detector data $Tf$ (generated by a system having all good detectors) from satisfying the H-L conditions. In other words, at least some of the H-L condition values will be non-zero for detector data generated by any real CT system.

It follows that the H-L condition values themselves do not individually indicate whether the CT system has a bad detector. However, the matrix (2.6) reveals that, for various values of $k$ and $m$, the H-L condition values form a well-defined pattern when a single detector channel goes bad. This pattern can be used to detect whether non-zero H-L condition values are the result of a bad detector, rather than merely global and computational errors.

Analyzing the form of matrix (2.6) for evidence of a bad detector begins with the realization that the global and computational errors will be distributed randomly in the detector data. Non-zero H-L condition values resulting from such errors will therefore appear with no identifiable pattern. In other words, if all the detectors are working properly, then the non-zero values in the matrix (2.6) will be distributed randomly in both magnitude and matrix position.

The expected values of such randomly distributed non-zero values can be estimated or measured directly from reliable scan data sets. The difference between a matrix of such expected values and the matrix (2.6) for measurement data can then be computed and compared in norm to an appropriate threshold value. Such a threshold value can be determined from the expected value matrix according to techniques well known in applied statistics.

The pattern shown in matrix (2.6) also provides an estimate for the location of the bad detector. As noted above, when the detectors are fixed with respect to the source, the fan position $\gamma_0$ uniquely determines the position of the bad detector. A value for $\gamma_0$ can be computed using equation (2.3):

$$\gamma^0 = \arcsin(E/D) \qquad (2.7)$$

The value E can be estimated from the entries of matrix (2.6), using the relationships between the entries thereof as noted above. For example, it is noted that for $|k|>m$, elements in each successive column are equal to the corresponding elements in the previous column, multiplied by E. Thus, taking ratios of corresponding elements in adjacent columns will result in estimates for E. A suitable value for E and the known distance D, when substituted into equation (2.7), yield an estimate for $\gamma_0$.

b. A Method and System for Signature Detection

Matrix (2.6) and equation (2.7) therefore provide a basis for detecting the presence and location of a bad CT detector from monitoring of the axial scan data. Referring again to the CT system 1 of FIG. 1, the monitoring system of the present invention can be implemented by configuring processing unit 210 to perform a monitoring routine for detecting the existence and location of a bad detector. For example, processing unit 210 may be configured in software for a programmable computer 250 to compute and analyze H-L condition values for axial scan data received from the detector array 140. Preferably, such a monitoring routine is performed in background, using cycles of processing unit 210 during which reconstruction unit 200 is not performing computations to reconstruct image data from axial scan data.

One implementation of a monitoring routine embodying the present invention will be described in detail below. If processing unit 210 determines, by executing the monitoring routine, that axial scan data contain the signature of a bad detector, then an appropriate notification signal is generated. For example, if processing unit 210 detects a bad-detector signature, then an alert signal AL may be sent to a communications interface 400 for transfer to a human operator. In one embodiment, interface 400 may send a warning message W to be presented to an operator of the CT system through display unit 300, either as a separate message or superimposed over visual presentation 310.

Alternatively, interface 400 may send warning message W to a technical support service provider (on-site or off-site). For example, warning message W may be incorporated in a voice or electronic message directed toward a telephony messaging server 410 at which the service provider is registered. Such a messaging server may allow the warning message to be delivered to the service provider by a human operator or by a synthesized or recorded voice message. Preferably the messaging server also allows the warning message to be delivered to a pager device carried by a technician or to a voice-mail inbox file for the service provider.

Similarly, warning message W may be incorporated in an electronic mail ("e-mail") message sent to an e-mail server 420 at the service provider is registered. Various other methods for directing an appropriate warning to a responsible party will be apparent from the foregoing examples.

In a further alternative embodiment, the monitoring system of the present invention is implemented to perform the monitoring routine utilizing a processor 510 separate from the processing unit 210 of the reconstruction unit 200. Such a separate processor 510 may be incorporated in the reconstruction unit 200 or may be included in a separate computer system (not shown) to which the axial scan data is transmitted. Further, either of processing unit 210 or processor 510 may be a general purpose processing unit, configured through software, or may be a special purpose computational unit including computational circuitry specific to the monitoring routine.

Figure 4:
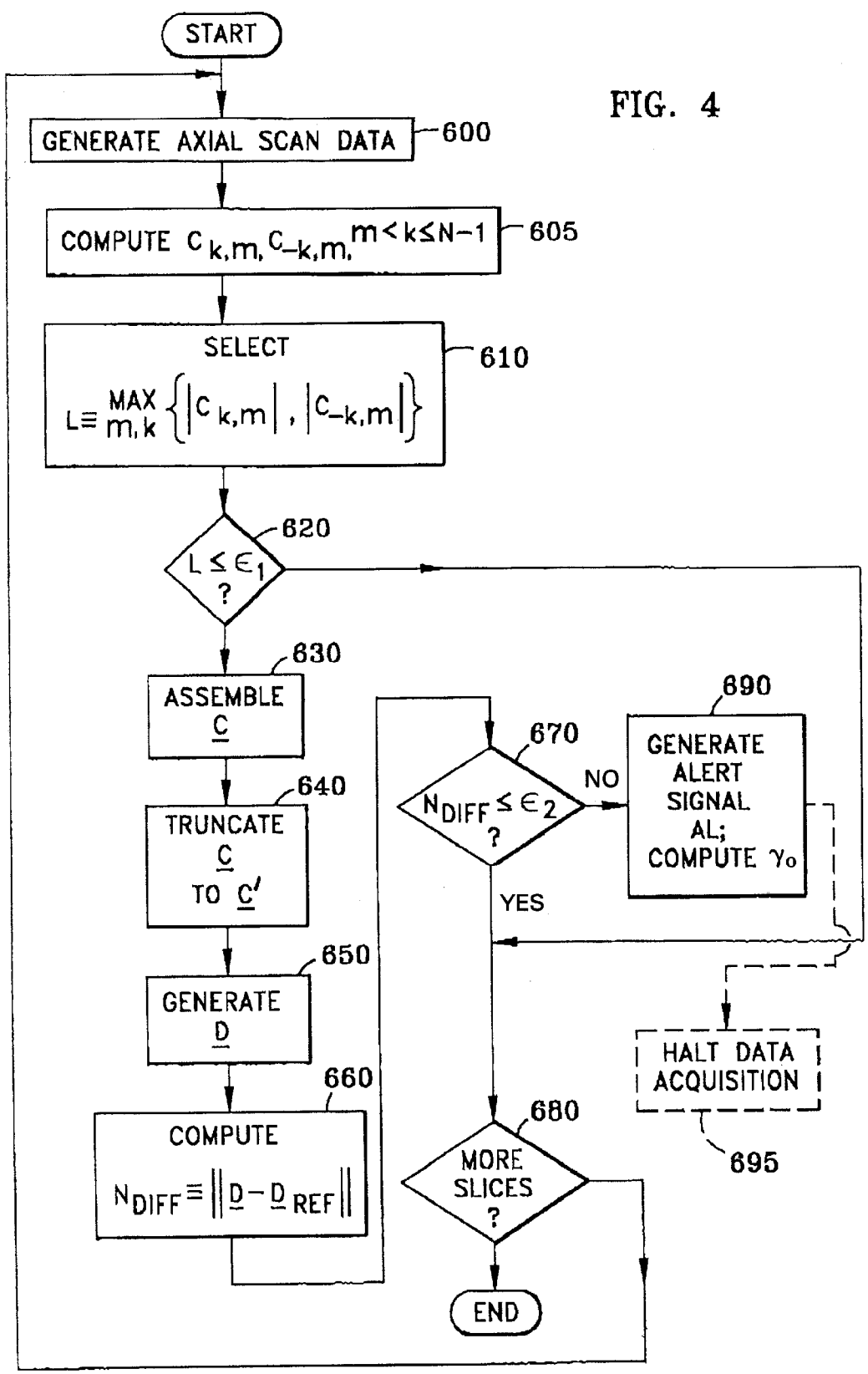
FIG. 4 illustrates a flow chart of a monitoring routine embodying the present invention.

One embodiment of the monitoring routine performed by the present invention is illustrated in the flow chart of FIG. 4. At the prefatory step 600, axial scan data are generated in the usual manner. Monitoring of the detector data for a bad detector signature begins at step 605, where H-L condition values $C_{k,m}$ and $C_{-k,m}$ are computed for $0 \leq m < k < N-1$. Here N is the number of distinct views in the axial scan data. For example, N=984 in the third-generation CT system of FIG. 1 with the exemplary system parameters noted above. $C_{k,m}$ and $C_{-k,m}$ are computed from Equation (1.7) above, using numerical quadrature routines well known in the computational arts.

At steps 610 and 620 an initial screening procedure is performed. First, at step 610, the largest value L among the $C_{k,m}$ and the $C_{-k,m}$ (in absolute value) is selected. At step 620, L is compared with a first threshold value $\in_1$. Here $\in_1$ is an empirically determined value selected according to system characteristics, as noted below.

If L exceeds $\in_1$ at step 620, then further analysis of the axial scan data is performed. First, a proper matrix $\underline{C}$ of the values $C_{k,m}$ and $C_{-k,m}$ is assembled, corresponding to the matrix of H-L values in Equation (2.6):

$$\underline{C} = \begin{bmatrix} C_{1,0} & 0 & 0 & \cdots \\ C_{-1,0} & 0 & 0 & \cdots \\ C_{2,0} & C_{2,1} & 0 & \cdots \\ C_{-2,0} & C_{-2,1} & 0 & \cdots \\ C_{3,0} & C_{3,1} & C_{3,2} & \cdots \\ C_{-3,0} & C_{-3,1} & C_{-3,2} & \cdots \\ \vdots & \vdots & \vdots & \cdots \end{bmatrix} \qquad (2.8)$$

Matrix $\underline{C}$ is a square matrix with N-1 rows and columns, the upper triangular elements (not given by Equation (2.6)) being set to zero.

Next, matrix $\underline{C}$ is truncated to form a square matrix $\underline{C}'$ having $K_{MAX}$ rows and columns. Here the truncation value $K_{MAX}$ is an integer less than N and is selected to provide adequate detection sensitivity for the monitoring routine while avoiding excessive computational load. A suitable value of $K_{MAX}$ can be chosen for a given CT system using standard methods from sampling theory, in the manner well known in the data sampling arts.

In view of the relationships given by Equations (2.4) and (2.5), a matrix $\underline{D}$ is formed at step 650 from matrix $\underline{C}'$ by defining $D_{k,m}=(C'_{k,m}/C'_{k,m-1}), {}^m \geq 1$:

$$\underline{D} = \begin{bmatrix} D_{2,1} & 0 & 0 & \cdots & 0 \\ D_{-2,1} & 0 & 0 & \cdots & 0 \\ D_{3,1} & D_{3,2} & 0 & \cdots & 0 \\ D_{-3,1} & D_{-3,2} & 0 & \cdots & 0 \\ \vdots & \vdots & \vdots & \cdots & \vdots \\ D_{R,1} & D_{R,2} & D_{R,3} & \cdots & D_{R,C} \\ D_{-R,1} & D_{-R,2} & D_{-R,3} & \cdots & D_{-R,C} \end{bmatrix} \quad (2.9)$$

It is noted that if the axial scan data are perfect, except for errors caused by a single bad detector, i.e., contain no systematic or computational errors, then $D_{k,m}|E$ for every k and m:

$$\underline{D} = \begin{bmatrix} E & 0 & 0 & \cdots & 0 \\ E & 0 & 0 & \cdots & 0 \\ E & E & 0 & \cdots & 0 \\ E & E & 0 & \cdots & 0 \\ E & E & E & \cdots & 0 \\ E & E & E & \cdots & 0 \\ \vdots & \vdots & \vdots & \vdots & \vdots \\ E & E & E & E & E \\ E & E & E & E & E \end{bmatrix} \quad (2.10)$$

In such a theoretical case, the existence of nonzero values in matrix $\underline{C}$ would conclusively indicate the presence of a bad detector, and the location of the bad detector could be computed directly from E using Equation (2.7). As noted above, various unavoidable systematic errors prevent this theoretical case from being achievable in practice.

To determine whether nonzero values in matrix $\underline{C}$ indicate the presence of a bad detector, the matrix $\underline{D}$ is modified by subtracting the expected contributions from such systematic errors. Thus, at step 660 a matrix norm $N_{DIFF}$ is computed for the difference matrix $\underline{D}-\underline{D}_{REF}$. $\underline{D}_{REF}$ is a matrix to estimate such expected systematic error contributions and is constructed to have the same block-triangular form as $\underline{D}$. The exact values of the expected contributions are difficult to estimate a priori, because the value of E depends on the location of the bad detector (see Equation 2.3). In the presently preferred embodiment, therefore, each non-zero entry of $\underline{D}_{REF}$ (corresponding to a non-zero entry of $\underline{D}$) is set to the average of the non-zero entries of $\underline{D}$.

The matrix norm is a scalar measure of the relative "size" of the difference matrix and is computed according to various techniques well known in the computational arts. In a preferred implementation, the so-called $L^2$ norm is used. Other matrix norms are well known and may be used, such as $L^1$ and $L^\infty$. Such alternative norms may be desirable where the distribution of values in the difference matrix has a distinctive pattern (e.g., predominantly row-oriented or column-oriented), and particularly where a less computationally demanding matrix norm is desired.

At step 670, matrix norm $N_{DIFF}$ is compared with a second threshold value $\in_2$. This second threshold comparison determines whether the nonzero H-L condition values in matrix $\underline{C}$ are likely caused by a bad detector. Both the first threshold value $\in_1$ and the second threshold value $\in_2$ will be selected according to characteristics of the particular CT system, in view of the fact that axial scan data sets include noise from the data acquisition equipment and will vary with dose level. The threshold values for the monitoring routine of the present invention are thus tuned to a specific CT system and generally are recalibrated on a periodic basis, as the system ages.

If $N_{DIFF}$ is found not to exceed the second threshold value $\in_2$ at step 670, then the routine flow proceeds directly to step 680 where it is determined whether further axial scan data sets ("slices") are to be analyzed. If so, then the flow returns to step 600 and a next axial scan data set is generated. The routine ends if no more slices are to be analyzed.

If $N_{DIFF}$ is found to exceed the second threshold value $\in_2$ at step 670, then the routine flow proceeds to step 680 where a notification signal such as the alert signal AL is generated to call attention to the likely existence of a bad detector. Also at step 680, an estimate for $\gamma_0$ will be generated using Equation (2.7). The value for E used in the computation of $\gamma_0$ may be, for example, an average of the individual elements of the difference matrix. After step 690, the routine flow may proceed to step 680.

The likely existence of a bad detector, as indicated by a violation of the second threshold condition at step 670, need not be interpreted as rendering useless all CT data from the system. Indeed, a substantial advantage of the monitoring system of the present invention resides in the fact that a bad detector may be identified early in the deterioration process. Such detection may occur before the data from that detector corrupts the axial scan data to a significant degree. Thus, a CT system incorporating the monitoring system of the present invention may desirably continue to generate axial scan data and CT images, even after the notification signal has been sent.

In an alternative embodiment, however, the monitoring system may be configured to suspend further CT scans until the detectors of the CT system are checked. Such an embodiment is illustrated by an alternate exit path from step 690 in FIG. 3, whereby the routine flow proceeds from step 690 to a step 695. Further data acquisition is halted at step 695, and the monitoring routine then ends without analyzing any additional axial scan data.

If L does not exceed $\in_1$ at step 620, then the routine flow proceeds directly to step 680. That is, further analysis of the axial scan data set can be skipped if the first, screening threshold condition is satisfied. This avoids the computations corresponding to steps 630–670 in the normal situation where all detectors are functioning properly and the computed H-L condition values are small.

3. Alternative Embodiments

FIGS. 1 and 4 illustrate the present invention in the context of a third-generation transmission CT system. As noted above, the third-generation system is configured with the source 120 and detector array 140 mounted on a gantry structure and rotated about an axis in fixed relation to one another. This configuration leads to the bad-detector model of Equation (2.1), with the bad detector located at fan position $\gamma_0$. The particular form of model (2.1) therefore carries the implicit assumption that To uniquely identifies the position of the bad detector. This implicit assumption in turn implies that the detector array is fixed with respect to the source (assuming the focal point of the source 120 is fixed with respect to the detector array 140).

Figure 5:
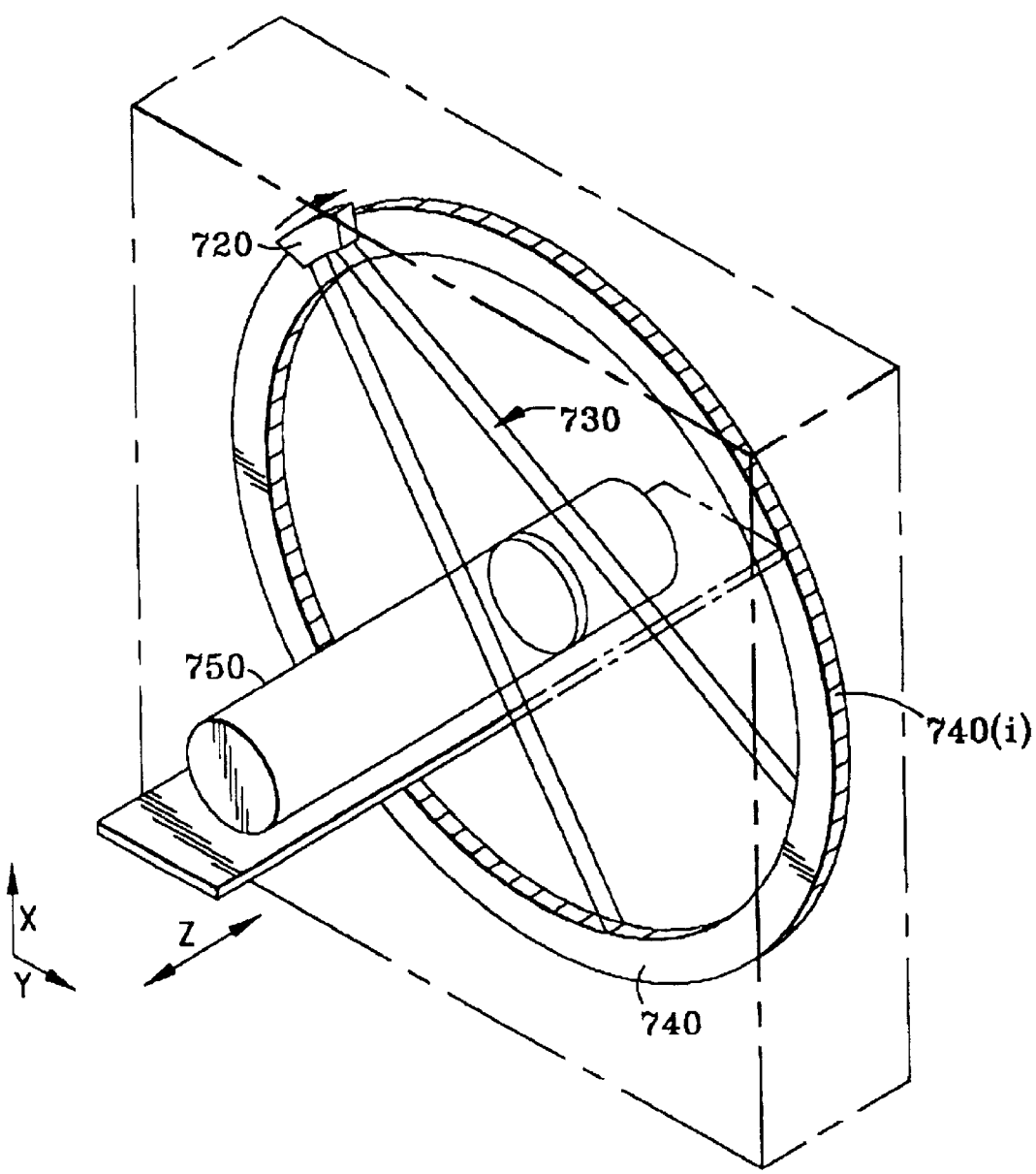
FIG. 5 is a perspective view of a CT scanner in accordance with one one embodiment of the present invention.

FIG. 5 shows a portion of a fourth-generation transmission CT system. Such fourth generation systems are expected to embody a detector-source configuration more advanced than the third-generation configuration illustrated in FIG. 1. In FIG. 5, source-collimator assembly 720 produces a fan beam 730. Assembly 720 is typically mounted on a gantry (not shown) analogous to the gantry 170 in FIG.

1. A detector array 740 comprises numerous detector elements 740($i$), which may be identical to the detector elements 140($i$) of the third generation system.

Unlike detector array 140, however, the fourth generation detector array 740 is fixed with respect to rotation about the subject aperture 750. That is, whereas source 120 and detector array 140 in FIG. 1 are fixed relative to one another, source 720 rotates relative to fixed detector array 740. In such an arrangement, the individual detector elements 740($i$) do not have fixed positions within the fan beam 730. It follows that the results of Section 2 above, which flow from model equation (2.1), are only indirectly applicable to the fourth generation case. That is, additional data manipulation is implemented to perform the background monitoring of the present invention on data generated by a fourth generation system.

The present invention can be applied to fourth generation systems by performing an additional prefatory step to re-bin the fourth generation data into third-generation format. Re-binning techniques are well known and are applied in, for example, U.S. Pat. No. 5,208,746, issued May 4, 1993, to King et al. The present invention can thus be implemented in fourth-generation CT systems as well as third-generation systems. The details of such fourth generation implementations will be apparent to those of skill in the art, in view of the present invention disclosure.

Further extensions of the invention will be apparent to those of skill in the art. For example, U.S. Pat. No. 4,812,983 discloses a technique for correcting CT scan data to compensate for a shift in the center of rotation of the detector-source assembly. Such a compensation procedure can be used as a prefatory operation in the monitoring routine of the present invention. The axial scan data sets can thus be suitably corrected for deviations in the center of rotation prior to the calculations outlined in FIG. 4. The present invention can also be extended to the case of multiple bad detectors interspersed in a detector array, as well as to detection of and compensation for z-axis errors.

As this invention may be embodied in several forms without departing from the spirit or essential characteristics thereof, the present embodiments are therefore illustrative and not restrictive. It will be appreciated by those skilled in the art that changes may be made to these embodiments without departing from the principles and spirit of the invention. Accordingly, the scope of the invention is defined by the appended claims rather than by the description preceding them, and all changes that fall within the metes and bounds of the claims, or equivalents of such metes and bounds thereof, are therefore intended to be embraced by the claims.

What is claimed is:

1. An apparatus for monitoring detector data of a CT system to detect a bad detector, said apparatus comprising:
   processing means for processing the detector data to generate a plurality of Helgason-Ludwig condition values, for generating a comparison value from the Helgason-Ludwig condition values, and for comparing the comparison value with a predetermined threshold value; and
   notifying means for generating a notification signal when the comparison value exceeds the predetermined threshold value.

2. The apparatus of claim 1, wherein said processing means further generates from the plurality of Helgason-Ludwig condition values an estimate of a position of the bad detector, when the comparison value exceeds the predetermined threshold.

3. The apparatus of claim 1, wherein the CT system is a third generation transmission computed tomography imaging system having a source of energetic signals and a detector array disposed in a fixed orientation relative to the source to receive the energetic signals as attenuated by an imaging object.

4. The apparatus of claim 1, wherein the detector data are axial scan data generated by the CT system in a tomographic scan operation.

5. The apparatus of claim 1, wherein:
   the CT system is a fourth generation transmission computed tomography imaging system having a source of energetic signals and a detector array, the source being rotatable about an imaging object and the detector array being rotationally fixed relative to the imaging object and receiving the energetic signals attenuated by the imaging object; and
   said processing means includes a unit to re-bin the detector data into an axial scan data set in a third generation CT system format.

6. The apparatus of claim 1, further comprising a communications interface coupled to said notifying means, said apparatus generating a warning message responsive to the notification signal and transmitting the warning message through said communications interface.

7. The apparatus of claim 6, wherein said communications interface transmits the warning message to at least one of a telephony messaging server and an e-mail server.

8. The apparatus of claim 1, wherein said processing means compares the absolute value of each of the Helgason-Ludwig condition values with a predetermined preliminary threshold value and generates the comparison value only when at least one of the absolute values exceeds the preliminary threshold value.

9. The apparatus of claim 1, wherein said processing means generates the comparison value by generating a first matrix of values, each corresponding to one of the Helgason-Ludwig condition values, and computing a matrix norm of the matrix of values as the comparison value.

10. The apparatus of claim 9, wherein said processing means generates the first matrix by:
    generating a truncated matrix of a selected subset of the plurality of Helgason-Ludwig condition values, the truncated matrix having a selected number of rows and a selected number of columns defining the selected subset;
    generating a second matrix of ratios of elements of the truncated matrix by dividing each element in a row and a second or succeeding column of the truncated matrix by an element in the row and an immediately preceding column of the truncated matrix; and
    subtracting a matrix of reference data elements from the second matrix to generate the first matrix.

11. The apparatus of claim 9, wherein said processing means compares the absolute value of each of the Helgason-Ludwig condition values with a predetermined preliminary threshold value and generates the first matrix only when at least one of the absolute values exceeds the preliminary threshold value.

12. The apparatus of claim 10, wherein:
    the detector data correspond to a predetermined number of views of an imaging object scanned by the CT system;
    the selected number of rows is less than the predetermined number of views; and
    the selected number of columns is equal to the selected number of rows.

13. A method for monitoring detector data of a CT system to detect a bad detector, the method comprising:
processing the detector data to generate a plurality of Helgason-Ludwig condition values, to generate a comparison value from the Helgason-Ludwig condition values, and to compare the comparison value with a predetermined threshold value; and
generating a notification signal when the comparison value exceeds the predetermined threshold value.

14. The method of claim 13, further comprising generating from the plurality of Helgason-Ludwig condition values an estimate of a position of the bad detector, when the comparison value exceeds the predetermined threshold.

15. The method of claim 13, wherein the CT system is a third generation transmission computed tomography imaging system having a source of energetic signals and a detector array disposed in a fixed orientation relative to the source to receive the energetic signals attenuated by an imaging object.

16. The method of claim 13, wherein the detector data are axial scan data generated by the CT system in a tomographic scan operation.

17. The method of claim 13, wherein:
the CT system is a fourth generation transmission computed tomography imaging system having a source of energetic rays and a detector array, the source being rotatable about an imaging object and the detector array being rotationally fixed relative to the imaging object; and
the method further includes re-binning the detector data into an axial scan data set in a third generation CT system format.

18. The method of claim 13, further comprising generating a warning message responsive to the notification signal and transmitting the warning message through a communications interface.

19. The method of claim 18, wherein the transmitting operation comprises transmitting the warning message to at least one of a telephony messaging server and an e-mail server.

20. The method of claim 13, further comprising comparing the absolute value of each of the Helgason-Ludwig condition values to a predetermined preliminary threshold value, and wherein the comparison value is generated only when at least one of the absolute values exceeds the preliminary threshold value.

21. The method of claim 13, wherein the comparison value is generated by generating a first matrix of values each corresponding to one of the Helgason-Ludwig condition values and computing a matrix norm of the first matrix as the comparison value.

22. The method of claim 21, wherein the first matrix is generated by:
generating a truncated matrix of a selected subset of the plurality of Helgason-Ludwig condition values, the truncated matrix having a selected number of rows and a selected number of columns defining the selected subset;
generating a second matrix of ratios of elements of the truncated matrix by dividing each element in a row and a second or succeeding column of the truncated matrix by an element in the row and an immediately preceding column of the truncated matrix; and
subtracting a matrix of reference data elements from the second matrix to generate the first matrix.

23. The method of claim 21, further comprising comparing the absolute value of each of the Helgason-Ludwig condition values with a predetermined preliminary threshold value, and wherein the first matrix is generated only when at least one of the absolute values exceeds the preliminary threshold value.

24. The method of claim 22, wherein:
the detector data correspond to a predetermined number of views of an imaging object scanned by the CT system;
the selected number of rows is less than the predetermined number of views; and
the selected number of columns is equal to the selected number of rows.

25. A computer readable medium encoded with a program for monitoring detector data of a CT system and detecting a bad detector by:
processing the detector data to generate a plurality of Helgason-Ludwig condition values, to generate a comparison value from the Helgason-Ludwig condition values, and to compare the comparison value with a predetermined threshold value; and
generating a notification signal when the comparison value exceeds the predetermined threshold value.

26. The computer readable medium of claim 25, wherein said program further comprises a procedure for generating from the plurality of Helgason-Ludwig condition values an estimate of a position of the bad detector, when the comparison value exceeds the predetermined threshold.

27. The computer readable medium of claim 25, wherein the CT system is a third generation transmission computed tomography imaging system having a source of energetic rays and a detector array disposed in a fixed orientation relative to the source.

28. The computer readable medium of claim 25, wherein the detector data are axial scan data generated by the CT system in a tomographic scan operation.

29. The computer readable medium of claim 25, wherein:
the CT system is a fourth generation transmission computed tomography imaging system having a source of energetic rays and a detector array, the source being rotatable about an imaging object and the detector array being rotationally fixed relative to the imaging object; and
said program further includes a procedure for re-binning the detector data into an axial scan data set in a third generation CT system format.

30. The computer readable medium of claim 25, wherein said program further comprises procedures for generating a warning message responsive to the notification signal and transmitting the warning message through a communications interface.

31. The computer readable medium of claim 30, wherein the transmitting procedure comprises at least one of a procedure for transmitting the warning message to a telephony messaging server and a procedure for transmitting the warning message to an e-mail server.

32. The computer readable medium of claim 25, wherein said program further comprises a procedure for comparing the absolute value of each of the Helgason-Ludwig condition values with a predetermined preliminary threshold value, and wherein the comparison value is generated only when at least one of the absolute values exceeds the preliminary threshold value.

33. The computer readable medium of claim 25, wherein said program generates the comparison value by generating a first matrix of values each corresponding one of the Helgason-Ludwig condition values and computing a matrix norm of the first matrix as the comparison value.

34. The computer readable medium of claim 33, wherein said program generates the first matrix by:

generating a truncated matrix of a selected subset of the plurality of Helgason-Ludwig condition values, the truncated matrix having a selected number of rows and a selected number of columns defining the selected subset;

generating a second matrix of ratios of elements of the truncated matrix by dividing each element in a row and a second or succeeding column of the truncated matrix by an element in the row and an immediately preceding column of the truncated matrix; and subtracting a matrix of reference data elements from the second matrix to generate the first matrix.

35. The computer readable medium of claim 33, wherein said program further comprises a procedure for comparing the absolute value of each of the plurality of Helgason-Ludwig condition values with a predetermined preliminary threshold value, and wherein said program generates the first matrix only when at least one of the absolute values exceeds the preliminary threshold value.

36. The computer readable medium of claim 25, wherein said program generates the comparison value by generating a first matrix of values each corresponding one of the Helgason-Ludwig condition values and computing a matrix norm of the first matrix as the comparison value.

37. The computer readable medium of claim 36, wherein said program generates the first matrix by:

generating a truncated matrix of a selected subset of the plurality of Helgason-Ludwig condition values, the truncated matrix having a selected number of rows and a selected number of columns defining the selected subset;

generating a second matrix of ratios of elements of the truncated matrix by dividing each element in a row and a second or succeeding column of the truncated matrix by an element in the row and an immediately preceding column of the truncated matrix; and subtracting a matrix of reference data elements from the second matrix to generate the first matrix.

38. The computer readable medium of claim 36, wherein said program further comprises a procedure for comparing the absolute value of each of the Helgason-Ludwig condition values with a predetermined preliminary threshold value, and wherein said program generates the first matrix only when at least one of the absolute values exceeds the preliminary threshold value.

39. The computer readable medium of claim 37, wherein:

the detector data correspond to a predetermined number of views of an imaging object scanned by the CT system;

the selected number of rows is less than the predetermined number of views; and the selected number of columns is equal to the selected number of rows.

40. A computed tomography system, comprising:

a detector array generating detector data responsive to energetic signals attenuated by a signal-absorbing body; and a computer including a processor processing the detector data to generate a plurality of Helgason-Ludwig condition values, generating a comparison value from the Helgason-Ludwig condition values, and comparing the comparison value with a predetermined threshold value; and said computer generating a notification signal when the comparison value exceeds the predetermined threshold value.

41. The system of claim 40, wherein the processor further generates from the plurality of Helgason-Ludwig condition values an estimate of a position of the bad detector, when the comparison value exceeds the predetermined threshold.

42. The system of claim 40, wherein:

said system is a third generation transmission computed tomography imaging system and further comprises a source of the energetic signals; and said detector array is disposed in a fixed orientation relative to said source.

43. The system of claim 40, wherein:

said system is a fourth generation transmission computed tomography imaging system comprising a source of the energetic signals, said source being rotatable about the signal-absorbing body and said detector array being rotationally fixed relative to the signal-absorbing body; and the processor re-bins the detector data into an axial scan data set in a third generation CT system format.

44. The system of claim 40, wherein:

said computer further comprises a communications interface; and said computer generates a warning message responsive to the notification signal and transmits the warning message through the communications interface.

45. The system of claim 40, wherein the processor compares the absolute value of each of the Helgason-Ludwig condition values with a predetermined preliminary threshold value and generates the comparison value only when at least one of the absolute values exceeds the preliminary threshold value.

46. The system of claim 40, wherein the processor generates the comparison value by generating a first matrix of values each corresponding to one of the Helgason-Ludwig condition values and computes a matrix norm of the matrix of values as the comparison value.

47. The system of claim 46, wherein the processor generates the first matrix by:

generating a truncated matrix of a selected subset of the plurality of Helgason-Ludwig condition values, the truncated matrix having a selected number of rows and a selected number of columns defining the selected subset;

generating a second matrix of ratios of elements of the truncated matrix by dividing each element in a row and a second or succeeding column of the truncated matrix by an element in the row and an immediately preceding column of the truncated matrix; and subtracting a matrix of reference data elements from the second matrix to generate the first matrix.

48. The system of claim 46, wherein the processor compares the absolute value of each of the Helgason-Ludwig condition values with a predetermined preliminary threshold value and generates the first matrix only when at least one of the absolute values exceeds the preliminary threshold value.

49. The system of claim 47, wherein:

the detector data correspond to a predetermined number of views of the signal-absorbing body;

the selected number of rows is less than the predetermined number of views; and the selected number of columns is equal to the selected number of rows.

* * * * *